United States Patent [19]
Lim et al.

[11] Patent Number: 5,972,688
[45] Date of Patent: Oct. 26, 1999

[54] HT$_{M4}$ METHODS OF TREATMENT AND ASSAYS, AGONISTS AND ANTAGONISTS

[75] Inventors: Bing Lim, Dorchester; Chaker N. Adra, Boston, both of Mass.; Jean-Michel Lelias, Columbus, Ohio

[73] Assignee: Beth Israel Deaconess Medical Center, Boston, Mass.

[21] Appl. No.: 08/994,578

[22] Filed: Dec. 19, 1997

Related U.S. Application Data

[60] Division of application No. 08/707,340, Sep. 3, 1996, Pat. No. 5,705,615, which is a continuation-in-part of application No. 08/675,648, Jul. 3, 1996, abandoned, which is a continuation-in-part of application No. 08/318,492, Oct. 6, 1994, Pat. No. 5,552,312.

[51] Int. Cl.$^6$ .............................. C12N 15/00; C12N 1/20; C07H 21/04
[52] U.S. Cl. .................................. 435/252.3; 435/320.1; 536/23.5
[58] Field of Search ........................ 536/23.5; 435/252.3, 435/320.1

[56] References Cited

FOREIGN PATENT DOCUMENTS

| | | |
|---|---|---|
| WO 95/05481 | 2/1995 | WIPO . |
| WO 95/33051 | 12/1995 | WIPO . |
| WO 96/01642 | 1/1996 | WIPO . |
| WO 96/01844 | 1/1996 | WIPO . |
| PCT/US97/15510 | 4/1998 | WIPO . |

OTHER PUBLICATIONS

Stedman's Medical Dictionary, 26th edition, Williams & Wilkins (Baltimore, MD), p. 613, 1995.

Hannon, Gregory J. et al., "KAP: A Dual Specificity Phosphatase that Interacts with Cyclin–Dependent Kinases," *Proc. Natl. Acad. Sci. USA*, vol. 91:1731–1735 (1994).

Rothe, Mike et al., "A Novel Family of Putative Signal Transducers Associated with the Cytoplasmic Domain of the 75 kDa Tumor Necrosis Factor Receptor," *Cell*, vol. 78:681–692 (1994).

Gyuris, Jeno et al., "Cdil, a Human G1 and S Phase Protein Phosphatase that Associates with Cdk2," *Cell*, vol. 75:791–803 (1993).

Shirakawa, Taro et al., "Association Between Atopy and Variants of the β Subunit of the High–affinity Immunoglobulin E Receptor," *Nature Genetics*, vol. 7:125–130 (1994).

Marsh, David G. and Meyers, Deborah A., "A Major Gene for Allergy—Fact or Fancy?," *Nature Genetics*, vol. 2:252–254 (1992).

Cookson, William O.C.M. et al., "Linkage Between Immunoglobulin E Responses Underlying Asthma and Rhinitis and Chromosome 11q," *The Lancet*, 1292–1295 (1989).

Ravetch, Jeffrey V. and Kinet, Jean–Pierre, "Fc Receptors," *Annu. Rev. Immunol.*, vol. 9:457–492 (1991).

Ra, Chisei et al., "Complete Structure of the Mouse Mast Cell Receptor for IgE (FcεRI) and Surface Expression of Chimeric Receptors (Rat–Mouse–Human) on Transfected Cells," *J. Biol. Chem.*, vol. 264 (26):15323–15327 (1989).

Maekawa, Kazuhiko et al., "Determination of the Sequence Coding for the β Subunit of the Human High–affinity IgE Receptor," *FEBS Lett.*, vol. 302(2):161–165 (1992).

Davies, Kevin, "Allergy by Mutation," *Nature*, vol. 369:506 (1994).

Küster, Helmut et al., "The Gene and cDNA for the Human Affinity Immunoglobulin E Receptor β Chain and Expression of the Complete Human Receptor," *J. Biol. Chem.*, vol. 267(18):12782–12787 (1992).

Mosialos, George et al., "The Epstein–Barr Virus Transforming Protein LMP1 Engages Signaling Proteins for the Tumor Necrosis Factor Receptor Family," *Cell*, vol. 80:389–399 (1995).

Poon, Randy Y.C. and Hunter, Tony, "Dephosphorylation of Cdk2 Thr$^{160}$ by the Cyclin–Dependent Kinase–Interacting Phosphatase KAP in the Absence of Cyclin," *Science*, vol. 270:90–93 (1995).

Kobayashi, Hirofumi et al., "Variability of 11q23 Rearrangements in Hematopoietic Cell Lines Identified with Fluorescence In Situ Hybridization," *Blood*, vol. 81(11):3027–3033 (1993).

Cookson, William O.C.M. et al., "Maternal Inheritance of Atopic IgE Responsiveness on Chromosome 11q," *The Lancet*, vol. 340(8816):381–384 (1992).

Ravetch, Jeffrey V., "Atopy and Fc Receptors: Mutation in the Message?," *Nature Genetics*, vol. 7:117–118 (1994).

Fields, Stanley and Song, Ok–kyu, "A Novel Genetic System to Detect Protein–Protein Interactions," *Nature*, vol. 340:245–246 (1989).

Yang, Xiaolu et al., "A Protein Kinase Substrate Identified by the Two–Hybrid System," *Science*, vol. 257:680–682 (1992).

Cheng, Genhong et al., "Involvement of CRAF1, A Relative of TRAF, in CD40 Signaling," *Science*, vol. 267:1494–1498 (1995).

Sebastian, Byron et al., "Cdc25M2 Activation of Cyclin–Dependent Kinases by Dephosphorylation of Threonine–14 and Tyrosine–15," *Proc. Natl. Acad. Sci. USA*, vol. 90:3521–3524 (1993).

Hakes, David J. et al., "A Protein Phosphatase Related to the Vaccinia Virus VH1 is Encoded in the Genomes of Several Orthopoxviruses and a Baculovirus," *Proc. Natl. Acad. Sci. USA*, vol. 90:4017–4021 (1993).

Harper, J.W. et al., "The P21 Cdk–Interacting Protein cip 1 is a Potent Inhibitor of G1 Cyclin–Dependent Kinases," *Cell*, vol. 75:805–816 (1993).

(List continued on next page.)

*Primary Examiner*—Karen Cochrane Carlson
*Assistant Examiner*—Holly Schnizer
*Attorney, Agent, or Firm*—Hamilton, Brook, Smith & Reynolds, P.C.

[57] ABSTRACT

The invention relates to a recombinant DNA molecule which encodes a HT$_{m4}$ protein, a transformed host cell which has been stably transfected with a DNA molecule which encodes a HT$_{m4}$ protein and a recombinant HT$_{m4}$ protein. The invention also relates to a method for detecting the presence of a hereditary atopy.

7 Claims, 2 Drawing Sheets

OTHER PUBLICATIONS

Kinet, Jean–Pierre et al., "Isolation and Characterization of cDNAs Coding for the β Subunit of the High–Affinity Receptor for Immunoglobulin E," *Proc. Natl. Acad. Sci. USA*, vol. 85:6483–6487 (1988).

Adra, Chaker N. et al., "Cloning of the cDNA for a Hematopoietic Cell–Specific Protein Related to CD20 and the β Subunit of the High–Affinity IgE Receptor: Evidence for a Family of Proteins With Four Membrane–spanning Regions," *Proc. Natl. Acad. Sci. USA*, vol. 91:10178–10182 (1994).

Galaktionov, Konstantin and Beach, David, "Specific Activation of cdc25 Tyrosine Phosphatases by B–Type Cyclins: Evidence for Multiple Roles of Mitotic Cyclins," *Cell*, vol. 67:1181–1194 (1991).

Wright, Mark D. and Tomlinson, Michael G., "The Ins and Outs of The Transmembrane 4 Superfamily," *Immunology Today*, vol. 15, No. 12:588–594 (1994).

Haas, Rainer et al., "Successful Autologous Transplantation of Blood Stem Cells Mobilized with Recombinant Human Granulocyte–Macrophage Colony–Stimulating Factor," *Experimental Hematology*, vol. 18:94–98 (1990).

Berardi, Anna C. et al., "Functional Isolation and Characterization of Human Hematopoietic Stem Cells," *Science*, vol. 267:104–108 (1995).

Huang, Shiang and Terstappen, Leon W.M.M., "Lymphoid and Myeloid Differentiation of Single Human CD34$^+$, HLA–DR$^+$, CD38$^-$ Hematopoietic Stem Cells," *Blood*, vol. 83, No. 6:1515–1526 (1994).

Fleming, William H. et al., "Functional Heterogeneity Is Associated with the Cell Cycle Status of Murine Hematopoietic Stem Cells," *J. of Cell Bio.*, vol. 122, No. 4:897–902 (1993).

Roberts, Andrew W. and Metcalf, Donald, "Noncycling State of Peripheral Blood Progenitor Cells Mobilized by Granulocyte Colony–Stimulating Factor and Other Cytokines," *Blood*, vol. 86, No. 4:1600–1605 (1995).

Reems, Jo Anna and Torok–Storb, Beverly, "Cell Cycle and Functional Differences Between CD34$^+$/CD38$^{hi}$ and CD34$^+$/38$^{lo}$ and Human Marrow Cells After In Vitro Cytokine Exposure," *Blood*, vol. 85, No. 6:1480–1487 (1995).

Takeuchi, Masahiro et al., "Anatomy of TRAF2," *J. of Bio. Chem.*, vol. 271, No. 33:19935–19942 (1996).

Rothe, Mike et al., "TRAF2–Mediated Activation of NF–+sc KB by TNF Receptor 2 and CD40," *Science*, vol. 269:1424–1427 (1995).

Barinaga, Marcia, "Forging a Path to Cell Death," *Science*, vol. 273:735–737 (1996).

Smith, Craig A. et al., "The TNF Receptor Superfamily of Cellular and Viral Proteins: Activation, Costimulation, and Death," *Cell*, vol. 76:959–962 (1994).

Cao, Zhaodan, et al., "TRAF6 is a Signal Transducer for Interleukin–1," *Nature*, vol. 383:443–446 (1996).

Ando, Kiyoshi et al., "Regulation of $G_1$/S Transition by Cyclins D2 and D3 In Hematopoietic Cells," *Proc. Natl. Acad. Sci. USA*, vol. 90:9571–9575 (1993).

Spangrude, Gerald J. et al., "Purification and characterization of Mouse Hematopoietic Stem Cells," *Science*, vol. 241:58–62 (1988).

Tanaka, Ryuhei et al., "Accelerated Cell–Cycling of Hematopoietic Progenitor Cells by Growth Factors," *Blood*, vol. 86, No. 1:73–79 (1995).

Tsai, Li–Huei et al., "The Cdk2 Kinase is Required for the G1–to–S Transition in Mammalian Cells," *Oncogene*, vol. 8:1593–1602 (1993).

Hohaus, Stefan et al., "Successful Autografting Following Myeloablative Conditioning Therapy with Blood Stem Cells Mobilized by Chemotherapy Plus rhG–CSF," *Experimental Hematology*, vol. 21:508–514 (1993).

Kobayashi, Hirofumi et al., "Fluorescence In Situ Hybridization Mapping of Translocations and Deletions Involving the Short Arm of Human Chromosome 12 in Malignant Hematologic Diseases," *Blood*, vol. 84, No. 10:3473–3482 (1994).

Sui, Xingwei et al., "gp130 and c–Kit Signalings Synergize for Ex Vivo for Expansion of Human Primitive Hemopoietic Progenitor Cells," *Proc. Natl. Acad. Sci.*, vol. 92:2859–2863 (1995).

Tedder, Thomas F. et al., "Isolation and Structure of a cDNA Encoding the B1 (CD20) Cell–surface Antigen of Human B Lymphocytes," *Proc. Natl. Acad. Sci.*, vol. 85:208–212 (1988).

Adra, Chaker N. et al., "HT$_{m4}$, A Four–Transmembrane Hematopoietic Specific Protein, Interacts With Tumor Necrosis Factor Associated Factor 2," *Blood Abstract 1350*, vol. 88, No. 10, suppl. 1 part 1–2:340A (1996).

Roy, A. et al., "Molecular Scanning of Human Diseases," *Singapore Journal of Obstetrics and Gynaecology*, vol. 26(3):176–186 (1993).

```
  1  GTG ATC TTT TCT GAG TGT CTC CTA CTT GCG ACA AGG TGG ACT TGG GAG GAA AGC CGT CTG       8
 61  CCA AAG CCT GAA GCC TCC AAG CCA TAA ACA ACC CCA ATG GCC TCC CAC GAA GTT GAT AAT      28
                                                           met ala ser his glu val asp asn 121  GCA GAG CTG GGG TCA GCC TCT GCC CAT GGT ACC CCA GGC AGT GAG ACG GGA CCA GAA GAG      48
     ala glu leu gly ser ala ser ala his gly thr pro gly ser glu thr gly pro glu glu 181  CTG AAT ACT TCT GTC TAC CAC CCC ATA AAT GGA TCA CCA GAT TAT CAG AAA GCA AAA TTA      68
     leu asn thr ser val tyr his pro ile asn gly ser pro asp tyr gln lys ala lys leu 241  CAA GTT CTT GGG GCC ATC CAG AAT CTG AAT GCA GCA ATG ATT CTG GCT CTG GGT GTC TTT      88
     gln val leu gly ala ile gln asn leu asn ala ala met ile leu ala leu gly val phe 301  CTG GGT TCC TTG CAA TAC CCA TAC CTT CAA AAG CAC TTC TTT TTC TTC ACC TTC TAC         108
     leu gly ser leu gln tyr pro tyr his gln lys his phe phe phe phe thr phe tyr 361  ACA GGC TAC CCG ATT TGG GGT GCT GTG TTT TTC TGT AGT TCA GGA ACC TTG TCT GTT GTA     128
     thr gly tyr pro ile trp gly ala val phe phe cys ser ser gly thr leu ser val val 421  GCA GGG ATA AAA CCC ACA AGA ACA TGG ATA CAG AAC AGT TTT GGA ATG AAC ATT GCC AGT     148
     ala gly ile lys pro thr arg thr trp ile gln asn ser phe gly met asn ile ala ser 481  GCT ACA ATT GCA CTA GTG GGG ACT GTT CTC TCA CTA TTT CTC TCA GAG TCA CCG GAC CTA TGC AAT TAC ATG GGC TCC    168
     ala thr ile ala leu val gly thr val leu ser leu phe leu ser glu ser pro asp leu cys asn tyr met gly ser 541  TCA TTA AGG AGT TGT CAC TCT CTA GTG TCT GTC CAC CTG ATT CTC CTC ACC TTG CTG GAA TTA TGC GTA ACT     188
     ser leu arg ser cys his ser leu val ser val his leu ile leu leu thr leu leu glu leu cys val thr 601  ATA TCA AAT GGC ATG GTG TCT CTA CTG AAT GCA AAC AAC TGC TGT AAT GCA AAC AGC TGC AAT TCC    208
     ile ser asn gly met val ser leu leu asn ala asn cys cys asn ala asn ser arg glu ile ser 661  ATC TCT ACC ATA GCC ATG TGG TGC AAT GCA AAC TGC TGT AAT GCA AAC AGC TGC AGA GAG ATT TCC
     ile ser thr ile ala met trp cys asn ala asn cys cys asn ser arg glu ile ser
```

FIGURE 1A

```
                                                                                     214
721  TCA CCT CCC AAT TCT GTG TAA TCA AGA ATA CCT CCT TAT GAA AAT AAT TCT GAG AGC ATG
     ser pro pro asn ser val END 781  AAT ATT TGA CCT GTA AAG CTC TAA ATC TCC AGT GAC TCA GAG CTT CAC CCA CAA ACT CAG GAG AAC ATA
841  AGC CTG CTC ACT CTA TCC TTT CTT AAT CCT TCC TCT ATC ATG GCA CCA ATC TTT GTG CGT GGG TTG GAC GTT
901  TGA CTG ACT ATA TTT CTT TAG GCA TTC TTG GAT ATC CTA TAA CTA ATC TGT AAC TTC AAC ATC TAT GAT CAT TAC GGA
961  AGG ACA GAT GTT TCC AGA AAT TGG TTC TAT TTC TTC TTA TCC ACC TAC TCC ATT GCT TTA TGA
1021 AAA GTT TTA AGG AAG GGC GGT ATA AAA CCT ATA ATC TTT CAA TAT TTT TCT AAA ATC CAA CTT
1081 GGT TTA AGG GAA TAG GAA TTA AAA TGA AAA ATT TTT ACA GAG AAA TGC TTC TTG
1141 CTG ACC GCC CAG TCA GCA AAA AAA GTG TCA GGA ATT ACA CCA TTA TCA TTA AAA
1201 ACT TTA ACA TCA ACT GTA TTT GAG ATG GGG TTA AAT AGG GAT TTA TGG CTC TGA GTC TGA GAG
1261 TAA ATT TTC ACT TCA CAC ATG TTT TCT CCC TGA GTA AAT GAC AAA CTC GAT TGT TAA AGA GAA CTA AAG AAT
1321 TGC TGG AAC TCA ATG TCT AGA ATC TGA AAG GAC TGG CAA ATT CTG AAA TTG TCA CTT ATT ACC TGT
1381 CAA GCC CAA TTT AGA ATC CAC ATC CAC CTC TCT AAT CTC TTT CTC ATC TGT AAA ATA GGT
1441 AAG GCC ATG TCT TGT AGA GGC AAA TTA TCT TTG GTT TCG GCT CTG AGG GTT AAA TGA AAA GAA AAT
1501 ATG AAC ATG GGC AAA ACT ACT ACA CAC TTG TCG AGT ACT CTC ATC TGT AAA TGA ATA GAA AAT
1561 GTA ATA ATA ACA CAC AGG TAC TTG AAA AAA AAA GTT AAA TAA AAA ATA GGT
1621 GTG AAA CAG CAG CAC CAC TTG AAA AAA AAA AA
```

HT$_{M4}$ METHODS OF TREATMENT AND ASSAYS, AGONISTS AND ANTAGONISTS

RELATED APPLICATIONS

This application is a divisional application of U.S. patent application Ser. No. 08/707,340, filed Sep. 3, 1996, issued Jan. 6, 1998 (U.S. Pat. No. 5,705,615) which is a continuation-in-part application of U.S. patent application Ser. No 08/675,648, filed Jul. 3, 1996, which is a continuation-in-part application of U.S. patent application Ser. No. 08/318,492, filed Oct. 6, 1994 now U.S. Pat. No. 5,552,312. The teachings of both applications are incorporated herein by reference in their entirety.

GOVERNMENT FUNDING

This invention was made with Government support under Grants DK44099 and CA42537 awarded by the National Institute of Health and Grant DE-FG02-86ER60408 from the Department of Energy. The Government has certain rights in the invention.

BACKGROUND OF THE INVENTION

Leukocyte cell-surface proteins are of crucial immunological importance in providing the cell with a means of sensing, responding and interacting with the environment. One class of such proteins is the superfamily of 4-transmembrane proteins (TM4SF) which consists of at least 15 members (e.g. CD9, CD37, CD53, CD63, CD81, CD82, A15) that are variously expressed on leukocytes. The existence of so many different TM4SF molecules, as well as their expression in organisms as diverse as humans and schistosomes, suggest a key role in biology. More recently, the cDNA for a prostate cancer metastasis protein has been cloned and is found to be related to the same family of protein. No clear function about this family of protein has emerged but accumulating evidence indicates that these proteins are likely to have important functions in regulation of cell proliferation and activation.

There is another family of 4-transmembrane proteins which are structurally distinct from TM4SF. Until recently, the only two known members of this family were the β-subunit of the high affinity IgE Fc receptor, Fc$_\epsilon$RIβ, and the B-cell specific antigen CD20.

Fc$_\epsilon$RI is part of a tetrameric receptor complex consisting of an α chain, a β chain and two γ chains (Kinet et al., *Proc. Natl. Acad. Sci. USA*, 15:6483–6487 (1988)). Together, they mediate interaction with IgE-bound antigens leading to dramatic cellular responses, such as the massive degranulation of mast cells. Thought until recently to be expressed only in mast cells and basophils, the high-affinity receptor Fc$_\epsilon$RI has been shown to be present also in Langerhans cells (Kinet, J. -P. et al., *Proc. Natl. Acad. Sci. USA* 85:6483–6487 (1988)), eosinophils (Sutton, B. J. and Gould, H. J., *Nature (London)* 366:421–428 (1993)) and peripheral monocytes. The β subunit, Fc$_\epsilon$RIβ, is a 4-transmembrane protein with both the amino and carboxyl termini residing in the cytoplasm.

Atopy is generally defined as a disorder of Immunoglobulin E (IgE) responses to common antigens, such as pollen or house dust mites. It is frequently detected by either elevated total serum IgE levels, antigen specific IgE response or positive skin tests to common allergens. In principle, atopy can result from dysregulation of any part of the pathway which begins with antigen exposure and IgE response to the interaction of IgE with its receptor on mast cells, the high affinity Fc receptor Fc$_\epsilon$RI, and the subsequent cellular activation mediated by that ligand-receptor engagement (Ravetch, *Nature Genetics,* 7:117–118 (1994)). Cookson et al., *Lancet,* 333:1292–1295 (1989) have reported a genetic link between generalized atopic IgE responses and a locus on human chromosome 11q.

Thus, FcRI plays a role in atopic diseases as well. Atopic diseases, which include allergy, asthma, atopic dermatitis (or eczema) and allergic rhinitis, together constitute one of the largest group of clinical disorders requiring medical intervention. In the United Kingdom alone, atopy gives rise to 3–5 million cases and as many as 2,000 deaths each year.

The human CD20 antigen (Tedder, T. F., et al., *Proc. Natl. Acad. Sci. USA* 85:208–212 (1988)), as well as its murine equivalent Ly-44 (Tedder, T. F. et al., *J. Immunol.* 141:4388–4394 (1988)), are expressed only in B-cells. Functional studies with different CD20 antibodies indicate that CD20 is involved in the regulation of B-cell activation (Clark, E. A. and Lane, J. L. *Annu. Rev. Immunol.* 9:97–127 (1991)). The CD20 protein also contains four transmembrane domains with the amino and carboxyl ends on the cytoplasmic side of the cell membrane. CD20 is believed to play a direct role in transmembrane Ca$^{-'}$ flux. It is not clear, however, whether CD20 alone is a channel protein, it functions as such in association with other proteins or it induces the activation of resident membrane channels.

SUMMARY OF THE INVENTION

The invention relates to compositions comprising HT$_{m4}$, agonists of HT$_{m4}$ and antagonists of HT$_{m4}$, antibodies which bind to HT$_{m4}$, methods of treatment with these products, methods of inhibiting binding of HT$_{m4}$, and methods of screening candidate agents for inhibition of HT$_{m4}$ interaction.

BRIEF DESCRIPTION OF THE DRAWINGS

FIGS. 1A and 1B depict the CDNA sequence of the HT$_{m4}$ gene and the amino acid sequence of the encoded protein. The nucleotide sequence is numbered on the left. The amino acid sequence of the longest open reading frame is numbered on the right beginning with the first presumed initiating methionine. An upstream in-frame stop codon, TAA, is indicated in bold letters at position 85. A TAA stop codon (END) is followed by a 3' untranslated region containing an AATAAA poly adenylation signal. The four putative transmembrane domains are underlined. Two phosphorylation sites are underlined with dotted lines.

DETAILED DESCRIPTION OF THE INVENTION

The invention relates to the discovery and cloning of the HT$_{m4}$ cDNA. The 1672-nucleotide long cDNA contains a long open reading frame, beginning at nucleotide position 97. The expression product of the cDNA is a 4 transmembrane spanning protein with a calculated molecular mass of about 25 kDa and 214 amino acids. The sequences are set forth in FIGS. 1A and 1B.

HT$_{m4}$ contains four hydrophobic domains of 20 to 21 amino acids. The amino terminal region before the beginning of the first hydrophobic domain contains four prolines. Each of the hydrophilic regions between the transmembrane segments contains a single proline. Several substrates for Casein kinase 2 phosphorylation (Pina, L. A. *Biochem. Biophys. Acta.* 1054:267–284 (1990)) of serine/threonine are found at residues 24 (TGPE), 155 (SSSE), 181 (TLLE), and 203 (SREE) and for Protein Kinase C phosphorylation at residue 149 (SLR). The sequence is consistent with a polypeptide chain that crosses the membrane four times, projecting two small loops extracellularly, and retaining the amino- and carboxyl-terminal portions in the cytoplasm.

$HT_{m4}$, as defined herein, encompasses an expression product which possesses one or more of the functions of the native protein, including signal transduction, cell growth, cell proliferation, transcription regulation, such as activation of a transcription factor, and mediation of an atopic disorder. Included are functional protein or polypeptide fragments and regions of the native protein and/or proteins or polypeptides where one or more amino acids have been deleted, added or substituted. Preferably, the protein or polypeptide shares at least about 50% homology and more preferably at least about 75% homology with the corresponding sequences of the native protein of FIGS. 1A and 1B. Also included are derivatives, including but not limited to fusion proteins and amino acid sequence variants of $HT_{m4}$.

Recombinant DNA molecules of the invention, in one embodiment, encode $HT_{m4}$, as defined herein. In one embodiment, the molecule shares at least about 50% homology, or sequence identity, and preferably at least about 75% homology (such as at least about 90% homology) with the corresponding sequences of the native gene, or fragment thereof, particularly in highly conserved regions of the 4-transmembrane protein family of $HT_{m4}$, CD20 and $Fc_{\epsilon}RI\beta$. Preferably, the recombinant DNA molecule comprises the corresponding encoding nucleotide sequences of FIGS. 1A and 1B.

In another embodiment recombinant DNA molecules, such as probes, can be employed, for example, to isolate genes encoding transmembrane proteins or receptors, such as the $Fc_{\epsilon}RI$. Such molecules comprise recombinant DNA molecules which hybridize, preferably selectively, to all of or a fragment of the sequences of FIGS. 1A and 1B. Preferably, the molecules hybridize under stringent conditions, such as those set forth in Sambrook et al. *Molecular Cloning: A Laboratory Manual,* 2nd Edition (Cold Spring Harbor Lab., Cold Spring Harbor, N.Y. (1989)). An example of stringent conditions can be a combination of temperature and salt concentration that is approximately 12°–20° C. below the calculated melting temperature of the hybrid. The temperature and salt conditions can often be determined empirically in preliminary experiments in which samples of genomic DNA immobilized on filters are hybridized to the probe and then washed. Id., at 9.50.

The recombinant DNA molecules can contain coding and non-coding sequences. Preferably, the molecules comprise at least about 25 nucleotides and more preferably at least about 60 nucleotides with 95–100% sequence identity to pull out gene. Preferably, DNA probes comprise sequences the same as or homologous to the corresponding region encoding the N- or C-termini of the protein.

The predicted structure of $HT_{m4}$ as discussed herein demonstrates the relationship of this protein to $Fc_{\epsilon}RI\beta$ and the CD20 antigen and provides evidence for a family of 4-transmembrane spanning proteins. The conservation of amino acids between all three proteins is highest in the four transmembrane domains. While much greater divergence exist in the hydrophilic amino and carboxyl termini, several amino acids within these regions are conserved such as the presence of 4 to 5 prolines in the amino terminus of all three proteins. Two conserved cysteine residues in the second extracellular domain between Tm-3 and Tm-4 suggest that intra- or inter-molecular di-sulphide bonds in this domain are present in all three proteins. $HT_{m4}$ also contains two phosphorylation sites (threonine[24] and serine[20.3]) in the cytoplasmic region of the protein. Finally, there is a highly conserved SSPP domain at the carboxyl end of all three proteins. The difference between CD20 and the other two proteins is contributed significantly by several long stretches of non-homologous amino acids. The carboxyl terminus of $Fc_{\epsilon}RI\beta$ contains the Reth or antigen receptor activation motif (ARAM) (Reth, M. *Nature (London)* 338:383–384 (1989)), which is not present in CD20 or $HT_{m4}$. The ARAM sequence is found in the cytoplasmic tail of several receptor subunits including CD3 γ, δ, ε and ζ, Igα and Igβ, in MB-1 and B29 antigen, and in the β and γ chain of $Fc_{\epsilon}RI$ (Weiss, A. and Littman, D. R. *Cell* 76:263–274 (1994)). Tyrosine residues in ARAM sequences are believed to be critical inducers of and substrates for phosphorylation by cytoplasmic tyrosine kinases, allowing for the recruitment of additional effector molecules (Weiss, A. and Littman, D. R. *Cell* 76:263–274 (1994); Paolini, R. et al., *Nature (London)* 353:855–858 (1991); Eiseman, E. and Bolen, J. B. *Nature (London)* 355:78–80 (1992)). The common exon-intron organization of the genes containing the ARAM sequence has led to the suggestion that they might have evolved from the same gene family (Weiss, A. and Littman, D. R. *Cell* 76:263–274 (1994)). However, the structural similarity of $Fc_{\epsilon}RI\beta$ to CD20 and $HT_{m4}$ suggests that the ARAM sequence was acquired by the $Fc_{\epsilon}RI\beta$ gene during evolution.

Chromosome mapping localized the $HT_{m4}$ gene to chromosome 11q12–13.1, the location of the CD20 gene. The murine $Fc_{\epsilon}RI\beta$ and the murine equivalent for CD20, Ly-44, are both located in the same position in mouse chromosome 19 (Tedder, T. F. et al., *J. Immunol.* 141:4388–4394 (1988); Clark, E. A. and Lane, J. L. *Annu. Rev. Immunol.* 9:97–127 (1991); Huppi, K. et al., *J. Immunol.* 143:3787–3791 (1989)). Therefore, the three genes are believed to have been originated and evolved from the same locus, further supporting the proposition that they are members of the same family of related proteins. They also form a family of proteins that is quite distinct from another large family of 4-transmembrane proteins related to TAPA-1(Fearon, D. T. *Curr. Op. Immunol.* 5:341–348 (1993); Barclay, A. N. et al., *The Leucocyte Antigen Facts Book*, (Academic Press Inc., San Diego, Calif.) (1993)) which include CD9, CD37, CD532, CD63 and R2.

The identification of a gene product like $HT_{m4}$ related to $Fc_{\epsilon}RI\beta$ is significant. While simultaneous cotransfection of the α, β and γ genes are necessary to induce surface expression of the murine $Fc_{\epsilon}RI$ receptor, cotransfection of the human α and γ genes without the β gene is sufficient to induce expression of high-affinity Fc receptors (Miller, L. et al., *Science* 244:334–337 (1989)). Furthermore, recent evidence indicated that functional high-affinity IgE Fc receptors can be found on monocytes in the absence of the β chain (Maurer, D. et al., *J. Exp. Med.* 179:745–750 (1994)).

Further, the diverse association of subunits in Fc receptors of different hematopoietic cells has been established. For example, $Fc_{\epsilon}RI\beta$ was found to be associated with the low-affinity Fc receptor for IgG, FcγRIII (CD16), in mast cells (Kurosaki, T. et al., *J. Exp. Med.* 175:447–451 (1992)). $Fc_{\epsilon}RI\gamma$ has also been found as a homodimer in association with FcγRIII in macrophages (Ra, C. et al., *Nature* 341:752–754 (1989)) or as a heterodimer with ζ and η chains in T cell receptor complex (Orloff, D. G. et al., *Nature* 347:189 (1990)). In NK cells, $Fc_{\epsilon}RI\gamma$ may be found as homodimers and as a heterodimer with the ζ-chain of T cell receptor (Letourneur, O. et al., *J. Immunol.* 147:2652–2656

(1991)). More recently others have shown that the γ chain can also form an association with the high-affinity receptor for IgG, FcγRI (CD64), in monocytic cell lines and neutrophils (Scholl, P. R. and Geha, R. S. *Proc. Natl. Acad. Sci. USA* 90:8847–8850 (1993); Ernst, L. K., et al., *Proc. Natl. Acad. Sci. USA* 90:6023–6027 (1993)). These findings suggest that a variety of signal transduction complexes composed of different subunits mediate similar effector functions but with different functional consequences. Association of these subunits with alternative ligand recognition subunits in a multimeric receptor complex would allow coupling of distinct ligands to common signaling pathways.

The expression of $HT_{m4}$ in all hematopoietic lineages and not in any of the non-hematopoietic cells tested indicates that $HT_{m4}$ participates in biochemical pathways unique to hematopoietic lineages.

Nucleic acids, such as DNA probes, comprising sequences of the genes encoding $HT_{m4}$ can be used in an assay to detect patients suffering from hereditary atopic disorders.

Either DNA or RNA can be used in the present assay method. The DNA which can be used in the method can be cDNA or genomic DNA. The source of DNA can be from any cell or cells removed from the individual and can include cultured progeny thereof, such as somatic cells, blood cells, sperm, fibroblasts or other somatic or germline cells. Also because the nucleic acid which is preferably analyzed is germline DNA, the method can be carried out prior or subsequent to onset of disease or disease symptoms. Where cDNA or RNA is to be used, the nucleic acid source should be from hematopoietic cells.

The presence of mutation can be determined using methods generally known in the art, such as by PCR (described herein below). Alternatively, the nucleic acid comprising the site of mutation or its complement can be sequenced, thereby identifying the presence of a mutation. In yet another embodiment, the protein encoded by the DNA can be sequenced or identified, thereby establishing the presence of the mutation. In yet another embodiment, an antibody which selectively binds to one of the mutated sequence or wild-type sequence can be made and used to screen a protein fraction for the respective proteins.

One such method is PCR methods using a pair of primers specific for sequence flanking the mutation region. The resulting products can be sequenced, analyzed on gels, such as polyacrylamide or agarose gels, or evaluated by physical characteristics such as melting temperature or secondary structure. Other methods for determining nucleic acid mutations or modifications can be employed, as well.

Co-amplification of two alleles in a heterozygote can generate PCR products which differ in the gene and therefore their melting and/or secondary structure characteristics are likely to differ. Under conditions as described in, e.g., Mutter and Boynton (Nucleic Acids Res. 23:1411 (1995)), amplification efficiency of the two alleles is near-equivalent, generating PCR products in a ratio proportional to that of the genomic template. Variability and biasing can be diminished by substitution of 7-deaza-2'-dGTP for dGTP during amplification, an intervention which reduces stability of intramolecular and intermolecular GC basepairing.

Allelic PCR fragments are easily separated, for example, by gel electrophoresis and detected by intercalating dye staining (e.g., ethidium bromide). As an alternative procedure, capillary electrophoresis can be employed. One example of capillary electrophoresis is in a polymer network consisting of 8% polyacryloylamino-ethoxyethanol in the absence of cross-linker, and offers a simple procedure for separation and on-line detection via UV absorbance at 254 nm, thus avoiding additional staining steps. The capillary column can be used repeatedly and the electropherogram can be stored on magnetic support. Comparisons among different runs can be obtained aligning all tracings to an internal standard of a known base pair size added as a marker (Nesi et al., Electrophoresis, 15:644–6 (1994)).

In yet another embodiment, the presence of a mutation can be determined according to the method of Yamamoto et al. (Biochem. Biophys. Res. Comm., 182:507 (1992)). The DNA or RNA obtained from the subject to be tested is amplified by standard PCR, a primer extension is carried out following addition of dideoxy ATP to the reaction mixture. The extension of the end-labeled reverse primer adjacent to the 3' end of the site of mutation stops at a selected nucleotide after the sequence to be tested and the resultant primer products can be analyzed by denaturing polyacrylamide gel electrophoresis and autoradiography.

Additional PCR based methods which can be used include random rapid amplification of cDNA ends (RACE), described by Carney et al. (Gene, 155:289, (1995)); single strand conformation polymorphism analysis (Ris-Stalpers et al., Pediatric Res., 36:227 (1994)) and reverse transcriptase PCR (Nakamura et al., J. Neurological Sci. 122:74 (1994)). Additional hybridization techniques include the use of probes labeled with the same or different radioactive or fluorescent dyes, for example. This method allows for the direct detection of a mutation or wild type sequences (see, e.g., Sanpei et al., Biochem. Biophys. Res. Comm. 212:341–6 (1995); Taneja, J. Cell Biology, 128:995–1002 (1995) and Saito, Japanese Journal of Human Genetics, 39:421–5 (1994)).

In yet another embodiment the protein which is encoded by the gene or fragment thereof, or in the alternative, the nucleic acid, can be separated by size using art-recognized separation media and methods. Standard polyacrylamide gels or a modified SDS-PAGE protocol using low concentration of methylenebisacrylamide and long runs (Ide et al., Biochem. Biophys. Res. Comm. 209:1119 (1995)).

The mutation associated with hereditary atopy can be identified by isolating and sequencing the $HT_{m4}$ gene of a population of individuals suspected of having hereditary atopy and of a population of individuals believed to not possess hereditary atopy. The sequences thus provided can be correlated and compared (e.g., obtaining consensus sequences or aligning sequences). "Mutation", as defined herein, is a consistent deviation in sequence shared by a population (or subpopulation thereof) of individuals suspected of having hereditary atopy, in comparison to the sequences found in the population (or subpopulation) of individuals believed to not possess hereditary atopy.

Also, the nucleic acids of the invention can be useful as probes to map genes on the human chromosome, such as employing the methods of fluorescence in situ hybridization (Kobayashi et al., *Blood,* 81:3027–3033 (1993)).

In addition, an animal model which has a genetic mutation in its genome such that functional $HT_{m4}$ is not encoded or expressed can be used to test drug targets. In one such example, the animal is immune-suppressed which can be used to screen drugs or drug targets that are otherwise possibly immunogenic.

In addition, the protein of the present invention can be used to screen for a native ligand.

MOLECULES THAT INTERACT WITH $HT_{m4}$

It has now been discovered that $HT_{m4}$ binds to two types of proteins, providing further information relating to the activation and inhibition of $HT_{m4}$ activity. One is a dual specificity phosphatase, call KAP, that is a tyrosine and serine/threonine dephosphorylating protein interacting with the cyclin-dependent kinase, CDK2. The other type of protein binds to the carboxyl terminal of the TNF receptor, Tumor Necrosis Factor Associated Factors TRAF-1, TRAF-2 and TRAF-3. They appear to be involved in signalling between receptors and transcriptional factors such as NF-κB and in the tumorigenicity of the EBV virus. Methods and assays that relate to enhancing and inhibiting the binding of these proteins to $HT_{m4}$ are also encompassed by the invention.

Dual-Function CDK2 Associated Phosphatase (KAP)

Dual-Function CDK2 associated phosphatase (KAP) is a mammalian cyclin-dependent kinase involved in cell cycling. The CDK2 protein regulates the cell cycle in G1 and S phase. See Hannon, G. J. et al., *Proc. Natl. Acad. Sci. USA*, 91: 1731–1735 (1994), Tsai, L -H, et al., *Oncogene*, 8:1593–1602 (1993), the teachings of which are incorporated herein by reference in their entirety. Co-immunoprecipitation experiments have shown that cyclin-dependent kinases bind a number of proteins in addition to cyclins. Galaktionov, K. et al., *Cell*, 67:1181–1194, Sebastian et al., *Proc. Natl. Acad. Sci. USA*, 90: 3521–3524(1993), Hakes, et al., *Proc. Natl. Acad. Sci. USA*, 90: 4017–4021 (1993), Harper, et. al. *Cell*, 74: 805–816 (1993) the teachings of which are incorporated herein by reference in their entirety. CDK Associated Protein (KAP) dephosphorylates not only phosphotyrosyl but also phosphoseryl, thus placing it in a class of so-called "dual function" phosphatases. It is believed that phosphatases, like KAP, play a critical role in regulating the level of phosphorylation of CDK proteins. Most recently, Poon et al. showed that the activation of cyclin-dependent kinases (CDKs) requires the phosphorylation of a conserved threonine ($Thr^{160}$ in CDK2) by CDK-activating kinase (CAK). *Science*, 270:90–93 (1995) the teachings of which are incorporated herein by reference in their entirety. Human KAP (also called Cdil) was shown to dephosphorylate threonine in human CDK2. KAP was unable to dephosphorylate tyrosine and dephosphorylated threonine in native monomeric CDK2. Heat denatured CDK2 was not dephosphorylated by KAP. The binding of cyclin A to CDK2 inhibited the dephosphorylation of $Thr^{160}$ by KAP but did not preclude the binding of KAP to the cyclin A-CDK2 complex. Furthermore, the dephosphorylation of Thr by KAP prevented CDK2 kinase activity upon subsequent association with cyclin A. These results suggest that KAP binds to CDK2 and dephosphorylates $Thr^{160}$ when the associated cyclin submit is degraded or dissociates.

Thus, KAP can inactivate a specific target protein kinase by removing phosphates in the activation loop and this ability is believed to constitute a general role for members of the dual specificity phosphatase family. The physiological importance of KAP is demonstrated by the observation that over-expression of KAP slows the progression of the pre-replicative $G_1$ phase of the cell cycle in HeLa cells. (Poon et al., Supra).

TNF Receptor Associated Factors (TRAF-1, TRAF-2 and TRAF-3)

TNF receptor associated factors (TRAF-1, TRAF-2 and TRAF-3) also bind with $HT_{m4}$. TRAF-2 is a protein that binds to the carboxyl terminus of the Tumor Necrosis Factor receptor-2 (TNF-R2). Rothe, M. *Cell*, 78:681–692 (1994), Mosialos, G. *Cell*,80:389–399 (1995), Cheng, G. et al., *Science*, 267: 1494–1498, the teachings of which are incorporated herein by reference in their entirety. TRAF-2 binds strongly with another related protein, TRAF-1, forming a heterodimeric complex that is associated with the cytoplasmic domain of Tumor Necrosis Factor Receptor, TNF-R2. TNF-R2 mediates TNF signalling, leading to stimulation of cell proliferation, mediation of gene induction and activation of transcription factors such as NF-κB. TRAF-1 and TRAF-2 are members of a protein family containing a C-terminal homology region designated "TRAF domain". Interestingly, in using a double hybrid yeast system to search for signalling proteins involved in interacting with the Epstein-Barr virus Transforming Protein, LMP1, a TRAF-2-like protein (now designated TRAF-3) was identified that binds to the cytoplasmic carboxyl terminal end of LMP1. Mosialos, supra. It is believed that LMP1 (a 6-transmembrane protein) expressed on infected cells, constitutively activates a cell proliferation pathway through TRAF-3 and TRAF-like proteins leading to transcription of NF-κB.

The association of $HT_{m4}$ with the dual function phosphatase, KAP, suggests that the activation of $HT_{m4}$ may involve phosphorylation. It also indicates that there might be a kinase that phosphorylates and activates $HT_{m4}$. Since KAP is a cell-cycle related phosphatase, $HT_{m4}$ may be involved in regulation of the cell cycle. The second protein, TRAF-2, that associated with $HT_{m4}$ suggests that $HT_{m4}$ may be important in the regulation of gene transcription, cell activation, cell proliferation and differentiation, inflammatory response, and apoptosis. Together, the new findings underscore the potential importance of the $HT_{m4}$ protein in regulating growth or activation of specific hematopoietic cells.

As noted above, $HT_{m4}$ is expressed preferentially in hematopoietic cells and the evidence thus far suggests that $HT_{m4}$ is a novel receptor protein, involved in a signalling pathway. It is significant that TNF which mediates pleiotropic functions including cell growth, cell activation and apoptosis, and LMP-1, which is a key EBV transforming protein, both utilize a similar pathway. Thus the TRAF proteins mediate critical signalling for cell growth.

Receptor cross-linking is believed to locally aggregate TRAF and associated molecules, thereby creating a second messenger signal, mediated by a receptor associated serine/threonine kinase, and manifested by phenotypic alterations, including the activation of transcription factor NF-κB and cell growth. A negative control of this pathway is believed to be dephosphorylation by a phosphatase.

Thus, it would be desirable to inhibit or activate $HT_{m4}$ activation, for example by inhibiting its binding to a native ligand of $HT_{m4}$, KAP, or TRAF-2, to modulate cell signalling and cell proliferation and transcription. Such modulation can occur through the screening, development and use of agonists and antagonists of $HT_{m4}$, including $HT_{m4}$ fragments, mutants, and antibodies.

Amino Acid Sequence Variants of Native $HT_{m4}$ Proteins or Fragments

Amino acid sequence variants of a native ligand of $HT_{m4}$ native ligand of a native ligand of $HT_{m4}$ native ligand of $HT_{m4}$ and $HT_{m4}$ fragments can be prepared by methods known in the art by introducing appropriate nucleotide changes into a native or variant $HT_{m4}$ DNA, or by in vitro synthesis of the desired polypeptide. There are two principal variables in the construction of amino acid sequence variants: the location of the mutation site and the nature of the mutation. With the exception of naturally-occurring alleles, which do not necessarily require the manipulation of the DNA sequence encoding $HT_{m4}$, the amino acid sequence variants of $HT_{m4}$ are preferably constructed by mutating the DNA, to arrive at an amino acid sequence variant that does not occur in nature.

Mutations can be created outside or within the $HT_{m4}$ domain or domains identified as being transmembrane, extracellular or intracellular, such as those involved in the interaction with a native ligand of $HT_{m4}$, TRAF-1, TRAF-2, TRAF-3 or KAP. $HT_{m4}$ variants mutated to enhance their association (binding or indirect association) with a native ligand of $HT_{m4}$, TRAF-1, TRAF-2, TRAF-3, or KAP and/or to retain their binding ability, preferably, while also reducing or eliminating their ability to signal NF-κB activation, will be useful as inhibitors of native biological activities mediated by a native ligand of $HT_{m4}$ TRAF-1, TRAF-2, TRAF-3, and/or KAP proteins. In addition, such variants, as well as native $HT_{m4}$ and binding fragments thereof, will be useful in the diagnosis of pathological conditions associated with the over-expression of those proteins, and in the purification of a native ligand of $HT_{m4}$, TRAF-1, TRAF-2, TRAF-3, or KAP. A preferred target for such mutations is the cytoplasmic carboxyl terminal domain, as this domain is believed to be involved in the interaction with TRAF-1, TRAF-2, TRAF-3 or KAP. Other amino acid sequence variants which act as inhibitors of $HT_{m4}$ biological activity can, for example, be identified by the biochemical screening assays described below.

In general, mutations can be conservative or non-conservative amino acid substitutions, amino acid insertions or amino acid deletions. The mutations can be at or near (within 5 or 10 amino acids) the $HT_{m4}$ binding sites (such as the TRAF-1, TRAF-2, TRAF-3 or KAP binding sites).

More preferably, DNA encoding a $HT_{m4}$ amino acid sequence variant is prepared by site-directed mutagenesis of DNA that encodes a variant or a nonvariant version of $HT_{m4}$. Site-directed (site-specific) mutagenesis allows the production of $HT_{m4}$ variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are will know in the art, as exemplified by publications such as Edelman et al., *DNA* 2, 183(1983). The site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well-known to those skilled in the art. A versatile and efficient procedure for the construction of oligonucleotide directed site-specific mutations in DNA fragments using M13-derived vectors was published by Zoller, M. J. and Smith, M., *Nucleic Acids Res.* 10. 6487–6500 [1982]). Also, plasmid vectors that contain a single-stranded phage origin of replication [Veira et al., *Meth. Enzymol.* 15, 3 (1987)] can be employed to obtain single-stranded DNA. Alternatively, nucleotide substitutions can be introduced by synthesizing the appropriate DNA fragment in vitro, and amplifying it by PCR procedures known in the art.

In general, site-specific mutagenesis herewith can be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer can then be annealed with the single-stranded protein sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector can then be used to transform appropriate host cells such as JP101 cells, and clones can be selected that include recombinant vectors bearing the mutated sequence arrangement. Thereafter, the mutated region can be removed and placed in an appropriate expression vector for protein production.

The PCR technique can also be used in creating amino acid sequences variants of a $HT_{m4}$. When small amounts for template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers can be designed to overlap the position of the mutation and to contain the mutation; the sequence of the other primer is preferably identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product can be used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

Another method for preparing variants, cassette mugenesis, is based on the technique described by Wells et al. [*Gene* 34, 315 (1985)]. The starting material can be the plasmid (or vector) comprising the $HT_{m4}$ DNA to be mutated. The codon(s) within the $HT_{m4}$ to be mutated are identified. There must be unique restriction endonuclease sites on each side of the identified mutation site(s). If such restriction sites do not exist, they can be generated using the above-described oligonucleotide-mediated mutagenesis method to introduce them at appropriate locations in the $HT_{m4}$ DNA. After the restriction sites have been introduced into the plasmid, the plasmid is cut at these sites to linearize it. A double stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designated to have 3' and 5' ends that are compatible with the ends of the linearized plasmid, such that it can be directly ligated to the plasmid. This plasmid now contains the mutated $HT_{m4}$ DNA sequence.

The $HT_{m4}$ protein variants, derivatives or fragments thereof can be employed in the preparation of antibodies, such as monoclonal antibodies, according to methods known in the art. The antibodies can be used to block or mimic ligand binding to the receptor comprising $HT_{m4}$ or other receptors, such as $Fc_{\epsilon}RI$, isolate the antibodies can be used to the $HT_{m4}$ protein or hematopoietic cells which contain the $HT_{m4}$ protein.

The antibodies can also be useful in the detection of hematopoietic cells in a sample. For example, the method comprises contacting the sample with the antibody under conditions sufficient for the antibody to bind to the $HT_{m4}$ protein and detecting the presence of bound antibody.

Antibodies and Methods

The term "antibody" is meant to include polyclonal antibodies, monoclonal antibodies (mAbs), chimeric antibodies, anti-idiotypic (anti-ID) antibodies to antibodies that can be labeled in soluble or bound form, as well as fragments, regions or derivatives thereof, provided by any known technique, such as, but not limited to, enzymatic cleavage, peptide synthesis or recombinant techniques. Anti-$HT_{m4}$ antibodies of the present invention are capable of binding the $HT_{m4}$ thereby inhibiting the binding of $HT_{m4}$ to one or more other proteins including a native ligand of $HT_{m4}$, TRAF-1, TRAF-2, TRAF-3 and KAP. Anti-TRAF-1, TRAF-2, or TRAF-3 and anti-KAP antibodies, and antibodies to a native ligand of $HT_{m4}$, of the present invention are capable of binding to TRAF-1, TRAF-2, TRAF-3 and KAP, and a native ligand of $HT_{m4}$, respectively, such that inhibition of binding the protein to $HT_{m4}$ occurs.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495–497 (1975); U.S. Pat. No. 4,376,110; Ausubel et al, eds., *CURRENT PROTOCOLS IN MOLECULAR BIOLOGY,* Green Publishing Assoc. and Wiley Interscience, N.Y., (1987, 1992); and Harlow and Lane *ANTIBODIES: A LABORATORY MANUAL* Cold spring Harbor Laboratory (1988); Colligan et al., eds., *CURRENT PROTOCOLS IN IMMUNOLOGY,* Greene Publishing Assoc. and Wiley Interscience, N.Y. (1992, 1993), the contents of which references are incorporated entirely herein by reference. Such antibodies can be of any immunoglobulin class including IgG, IgM, IgE, IgA, GILD and any subclass thereof. A hybridoma producing a mAb of the present invention can be cultivated in vitro, in situ or in vivo. Production of high titers of mAbs in vivo or in situ makes this the presently preferred method of production.

Chimeric antibodies which include humanized antibodies, are molecules different portions of which are derived from different animal species, such as those having variable regions derived from a murine mAb and a human immunoglobulin constant region. Chimeric antibodies are primarily used to reduce immunogenicity in application and/or to increase yields in production, for example. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 1739494 (published Mar. 5, 1986); Neugerger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066–1074 (1986); Robinson et al., Internation Patent Publication #PCT/US86/02269 (published May 7, 1987); Liu et al., Proc. Natl. Acad. Sci. USA 84:3439–3443 (1987); Sun et al., Proc. Natl., Acad. Sci. USA 84:214–218 (1987); Better et al., Science 240:1041–1043 (1988); and Harlow and Lane *ANTIBODIES: A LABORATORY MANUAL* Cold Spring Harbor Laboratory (1988)). These references are entirely incorporated herein by reference.

An anti-idiotypic (anti-Id) is an antibody which recognizes unique determinants generally associated with the antigen-binding site of an antibody. An anti-Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb it is possible to identify other clones expressing antibodies of identical or substantially identical specificity.

Antibodies of the present invention can include at least one of a heavy chain constant region ($H_c$), a heavy chain variable region ($H_v$), a light chain variable region ($L_v$) and a light chain constant regions ($L_c$), wherein a polyclonal Ab, monoclonal Ab, fragment and/or regions thereof include at least one heavy chain variable region ($H_v$) or light chain variable region ($L_v$) which binds a portion of the desired antigen and inhibits and/or neutralizes at least one biological activity.

Preferred antibodies of the present invention are high affinity anti-$HT_{m4}$ antibodies, and fragments or regions thereof, that have potent inhibiting and/or neutralizing activity in vivo against human $HT_{m4}$. Such antibodies can include those generated by immunization using purified recombinant $HT_{m4}$ or peptide fragments thereof. Preferred antibodies are these that bind to epitopes in the non-transmembrane domains of $HT_{m4}$. Especially preferred are antibodies which bind to epitopes in the extracellular domains between the first and second transmembrane domains and between the third and fourth transmembrane domains. Also preferred are fragments which include epitopes or residues located in amino acids 193–214 of SEQ ID NO:4.

Preferred anti-$HT_{m4}$ mAbs are also those which will competively inhibit in vivo the binding to $HT_{m4}$ by a native ligand of $HT_{m4}$, TRAF-1, TRAF-2, TRAF-3, KAP, or an antibody having substantially the same specific binding characteristics, as well as fragments and regions thereof. Preferred antibodies of the present invention are also those that bind epitopes recognized by TRAF-1, TRAF-2, TRAF-3 and KAP, which are included in amino acids 193–214 of SEQ ID NO:4.

Also preferred are anti-$HT_{m4}$ antibodies which bind the phosphorylation site in the cytoplasmic carboxyl terminal domain to inhibit binding of $HT_{m4}$ to KAP.

Preferred methods for determining mAb specificity and affinity by competitive inhibition can be found in Harlow, et al., *Antibodies: A Laboratory Manual,* Cold Spring Harbor Laboratory Press, Cold Spring Harbor, N.Y., 1988), Colligan et al, eds., *Current Protocols in Immunology,* Greene Publishing Associ. and Wiley Interscience, N.Y., (1992, 1993), and Muller, *Meth. Enzymol.,* 92:589–601 (1983), which references are entirely incorporated herein by reference.

The techniques to raise antibodies of the present invention to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art.

As used herein, the term "antigen-binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

Preferably, the antigen binding region will be of murine origin. In other embodiments, the antigen binding regions can be derived from other animal species, in particular rodents such as rabbit, rat or hamster.

The antigen binding region of the chimeric antibody of the present invention is preferably derived from a non-human antibody specific for the human protein of interest. Preferred sources for the DNA encoding such a non-human antibody include cell lines which produce antibodies, preferably hybrid cell lines commonly known as hybridomas.

An "antigen" is a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

Particular peptides which can be used to generate antibodies of the present invention can include $HT_{m4}$ residues 193–214 of SEQ ID NO:4, and fragments of $HT_{m4}$ which comprise the non-transmembrane domains of $HT_{m4}$, such as the extracellular domains between the first and second transmembrane domains and between the third and fourth transmembrane domains. Fragments or combinations of peptides contained therein, which provide an epitope of $HT_{m4}$ that is bound by anti-$HT_{m4}$ antibodies, fragments and regions thereof, and which binding provided anti-$HT_{m4}$ biological activity.

The term "epitope" is meant to refer to that portion of any molecule capable of being recognized and bound by an antibody at one or more of the Ab's antigen binding regions. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule or organism containing the epitope, in vivo, in vitro or in situ, more preferably in vivo, including binding of $HT_{m4}$ to a $HT_{m4}$ ligand or other binding protein.

Epitopes recognized by antibodies, and fragments and regions thereof, of the present invention can comprise at least one amino acid of residues 193–214 of $HT_{m4}$, or of a residue located within the non-transmembrane domains of $HT_{m4}$, such as the extracellular domains between the first and second transmembrane domains and between the third and fourth transmembrane domains which provide a topographical or three dimensional epitope of $HT_{m4}$ which is recognized by, and/or binds with anti-$HT_{m4}$ activity, and antibody, and fragments, and variable regions thereof, of the present invention.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimer associated through at least one disulfide bridge. A polyvalent chimeric antibody can also be produced, for example, by employing a $C_H$ region that aggregates (e.g., from an IgM H chain, or $\mu$ chain).

Murine and chimeric antibodies, fragments and regions of the present invention comprise individual heavy (H) and/or light (L) immunoglobulin chains. A chimeric H chain comprises an antigen binding region derived from the H Chain of a non-human antibody specific for the antigen, which is linked to at least a portion of a human H chain C region ($C_H$), such as $CH_1$ or $CH_2$.

A chimeric L chain according to the present invention, comprises an antigen binding region derived from the L chain of a non-human antibody specific for $HT_{m4}$, linked to at least a portion of a human L chain C region ($C_L$).

Antibodies, fragments or derivatives having chimeric H chains and L chains of the same or different variable region binding specificity, can also be prepared by appropriate association of the individual polypeptide chains, accordingly to known method steps, e.g., according to Ausubel infra, Harlow infra, and Colligan infra, the contents of which references are incorporated entirely herein by reference.

With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

The hybrid cells are formed by the fusion of a non-human anti-$HT_{m4}$ antibody-producing cell, typically a spleen cell of an animal immunized against either natural or recombinant $HT_{m4}$, or a peptide fragment of the human $HT_{m4}$ protein sequence. Alternatively, the non-human anti-$HT_{m4}$ antibody-producing cell can be a B lymphocyte obtained from the blood, spleen, lymph nodes or other tissue or an animal immunized with $HT_{m4}$.

The second fusion partner, which provides the immortalizing function, can be a lymphoblastoid cell or a phlasmacytoma or myeloma cell, which is not itself an antibody producing cell, but is malignant. Preferred fusion partner cells include the hybridoma SP2/0-AG14, abbreviated as SP2/0 (ATCC CRL1581) and the myeloma P3X63Ag8 (ATCC TIB9), or its derivatives. See, e.g, Ausubel infra, Harlow infra, and Colligan infra.

Murine hybridomas which produce mAb specific for $HT_{m4}$ are formed by the fusion of a mouse fusion partner cell, such as SP2/0, and spleen cells from mice immunized against purified $HT_{m4}$, recombinant $HT_{m4}$, natural or synthetic $HT_{m4}$ peptides, including peptides including amino acids selected from residues 193–214 of $HT_{m4}$ of SEQ ID NO:4 or other biological preparations containing $HT_{m4}$ . To immunize the mice, a variety of different conventional protocols can be followed. For example, mice can receive primary and boosting immunizations of $HT_{m4}$.

The antibody-producing cell contributing the nucleotide sequence encoding the antigen-binding region of the chimeric antibody of the present invention can also be produced by transformation of a non-human, such as a primate, or a human cell. For example, a B-lymophocyte which produces anti-$HT_{m4}$ antibody can be infected and transformed with a virus such as Epstein-Barr virus to yield an immortal anti-$HT_{m4}$ producing cell (Kozbor et al. *Immunol. Today* 4:72–29 (1983)). Alternatively, the B-lymphocyte can be transformed by providing a transforming gene product, as is well-known in the art. See, e.g. Ausubel infra, Harlow infra, and Colligan infra.

Antibody Production Using Hybridomas

The cell fusions are accomplished by standard proecedures well known to those skilled in the field of immunology. Fusion partner cell lines and methods for fusion and selecting hybridomas and screening for mAbs are well known in the art. See, e.g., Ausubel infra, Harlow infra, and Colligan infra.

The $HT_{m4}$-specific murine or chimeric mAb of the present invention can be produced in large quantities by injecting hybridoma or transfectoma cells secreting the antibody into the peritoneal cavity of mice and, after an appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

Fragments include, for example, Fab, Fab', F(ab'), and Fv. These fragments lack the Fc fragment of an intact antibody, clear more rapidly from the circulation, and can have less non-specific tissue binding than an intact antibody (Wahl et al., *J. Nucl. Med.* 24:316–325 (1983)). These fragments are produced from intact antibodies using methods well known in the art, for example by proteolytic cleavage with enzymes such as papain (to produce Fab fragments) or pepsin (to produce $F(ab')_2$ fragments).

Methods of Treatment

This invention also pertains to methods of treating an $HT_{m4}$-mediated disease, such as atopy and tumors, in an individual comprising administering an antagonist of $HT_{m4}$ to the individual. The antagonist can inhibit the activity of the $HT_{m4}$ gene or protein, causing inhibition of, for example, cellular DNA replication or proliferation. As used herein, inhibition of tumor cell DNA replication includes decreasing the rate of frequency of DNA replication as well as completely preventing DNA replication. Also, as defined herein, inhibition of tumor growth of the subject includes stopping the growth of the tumor and decreasing the size of the tumor.

$HT_{m4}$ antagonists include compounds which block at least one biological activity of $HT_{m4}$, such as preventing $HT_{m4}$ from binding to a native ligand of $HT_{m4}$, TRAF-1, TRAF-2, TRAF-3, or KAP, blocking production of $HT_{m4}$ by intracellular processing, such as transcription, translation or post translational modification, expression on the cell surface, secretion or assembly of $HT_{m4}$. Additionally, $HT_{m4}$ antagonists can act by inducing or enhancing regulation of metabolic pathways such as those involving up or down regulation of $HT_{m4}$ production, both at the nucleic acid and protein levels. Alternatively, $HT_{m4}$ antagonists can modulate cellular sensitivity to $HT_{m4}$ by decreasing such sensitivity. $HT_{m4}$ antagonists include antibodies, or fragments or portions thereof, peptides, peptido mimetic compounds or organo mimetic compounds that neutralize $HT_{m4}$ activity in vitro, in situ or in vivo. Screening methods which can be used to determine TNF neutralizing or inhibiting activity of a $HT_{m4}$ antagonist can include in vitro or in vivo assays.

Accordingly, any suitable $HT_{m4}$ antagonist can be used in methods according to the present invention. Examples of such $HT_{m4}$ antagonists include antibodies or portions thereof specific to epitopes of $HT_{m4}$ a native ligand of $HT_{m4}$, KAP or TRAF-1, TRAF-2, TRAF-3, non-activating ligands of $HT_{m4}$ peptides which bind $HT_{m4}$, peptido mimetics and organo mimetics that block $HT_{m4}$.

The invention pertains to novel methods and products for blocking cell proliferation in disorders, including but not limited to, cancer, atherosclerotic vascular disease, vascular restenosis following medical or surgical reperfusion procedures, psoriasis, inflammatory arthritis and other inflammatory diseases, autoimmune diseases, Epstein-Barr virus and rejection of transplanted organs.

Accordingly, the present invention provides methods of inhibiting undesirable cell proliferation in an individual comprising administering an antagonist of $HT_{m4}$ to the individual in such a manner that the antagonist enters the cells, where appropriate, in which it is desirable to inhibit proliferation. An antagonist of $HT_{m4}$ will prevent or reduce the activity of $HT_{m4}$ and thereby prevent the replication of cellular DNA. In other embodiments, antagonists of $HT_{m4}$ will prevent or reduce the activity of $HT_{m4}$ in mediating the symptoms of hereditary atopy.

In addition, the ability of $HT_{m4}$ to initiate DNA replication can be exploited to enhance cell proliferation for therapy of conditions associated with loss of viable tissue in an individual, including but not limited to, traumatic injury, myocardial infarction, cardiomyopathy, renal failure, hepatic failure and stroke. For example, this invention provides a method of enhancing cell proliferation for therapy of a condition associated with loss of viable tissue in an individual comprising administering $HT_{m4}$ or an agonist of $HT_{m4}$ to an individual such that it enters cells in the individual.

As used herein, the term "agonist" of $HT_{m4}$ means a molecule or composition which mimics or enhances the function or activity of $HT_{m4}$ or which prevents or inhibits the down-regulation or decrease in expression of $HT_{m4}$, both at the DNA or RNA (nucleic acid) and protein (amino acids) levels For instance, agonists of $HT_{m4}$ include kinases and anti-KAP antibodies, a native ligand of $HT_{m4}$, or molecules which mimic the function of the ligand. The activity of $HT_{m4}$ or an $HT_{m4}$ agonist causes initiation of DNA replication in the cell and entry of the cell into mitosis. Administration of $HT_{m4}$ or an $HT_{m4}$ agonist can supplement, enhance or replace the naturally-occurring levels of $HT_{m4}$ and enhance cell proliferation.

$HT_{m4}$ and $HT_{m4}$ agonists and antagonist of the present invention can be administered either as individual therapeutic agents or in a composition with other therapeutic agents.

They can be administered alone, but are generally administered in a composition with a physiologically compatible pharmaceutical carrier selected on the basis of the chosen route of administration and standard pharmaceutical practice.

In this context, drugs designed on the basis of the $HT_{m4}$ protein sequence and intended for use in humans include small non-peptide molecules, peptides or proteins related to $HT_{m4}$ or designed to alter the function of endogenous $HT_{m4}$, or DNA or RNA sequences encoding proteins or peptides related to $H_{m4}$ or designed to alter the function of endogenous $HT_{m4}$.

The dosage administered will, of course, vary depending upon known factors such as the pharmacodynamic characteristics of the particular agent, and its mode and route of administration; age, health, and weight of the a recipient; nature and extent of symptoms, kind of concurrent treatment, frequency of treatment, and the effect desired.

The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of the agent at the site of treatment include, but are not limited to, intradermal, intramuscular, intraperitoneal, intravenous, subcutaneous, oral, intranasal and gene therapy. Other suitable methods include or employ biodegradable devices and slow release polymeric devices.

Because proteins are subject to being digested when administered orally, parenteral administration, e.g., intravenous, subcutaneous, intramuscular, would ordinarily be used to optimize absorption.

For parenteral administration, $HT_{m4}$ agonists or $HT_{m4}$ antagonists, can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques. Suitable pharmaceutical carriers are described in the most recent edition of Remington's Pharmaceutical Sciences, A. Osol, a standard reference text in this field of art.

One preferred embodiment is a composition comprising an $HT_{m4}$ antagonist having potent in vivo $HT_{m4}$-inhibiting and/or neutralizing activity, accordingly to the present invention, that blocks $HT_{m4}$-induced cell growth or proliferation, or $HT_{m4}$-induced activation of a transcription factor. Another preferred use is a composition comprising $HT_{m4}$ or a $HT_{m4}$ agonist, which is capable of inducing cell growth or cell proliferation, or activating a transcription factor such as NF-κB.

Methods of Screening Agonists and Antagonists The invention further relates to a method of screening modulators, e.g., agonists and antagonists, of $HT_{m4}$. The method comprises contacting $HT_{m4}$ (including native $HT_{m4}$, active fragments or variants thereof) with a binding partner, such as a ligand or compound which binds $HT_{m4}$ (including KAP, TRAF-1, TRAF-2, TRAF-3, and native ligands, including the native proteins, active fragments or variants thereof), in the presence of a compound to be screened. The method further comprises the detection of the presence or absence of binding. Agonists and antagonists detected by the present method can be used, for examples, in vitro, or in the methods of therapy described above.

In one embodiment, the method comprises screening inhibitors or antagonists of $HT_{m4}$ comprising contacting $HT_{m4}$ with a native ligand of $HT_{m4}$, TRAF-1, TRAF-2, or TRAF-3 in the presence of the compound to be screened and detecting the presence or absence of binding. The compound can be located in a chemical library. Inhibition of binding can be detected in a number of ways. For example, either $HT_{m4}$ a native ligand of $HT_{m4}$, TRAF-1, TRAF-2, or TRAF-3 can be labeled, immobilizing the other with detection of label upon the immobilized substrate directly (as in a radiolabel) or in a coupled assay, as is known in the art. In another example, the inhibition can be detected by observing the absence or inhibition of a native ligand, TRAF-1, TRAF-2, or TRAF-3 activity, such as the absence of NF-κB activity. In yet another embodiment, the inhibition can be determined by observing decreased cell proliferation.

In yet another embodiment, a method for screening inhibitors or antagonists of $HT_{m4}$ comprises contacting $HT_{m4}$ with KAP and detecting the presence of binding or KAP dephosphorylation activity. Similarly to the above methods, either $HT_{m4}$ or KAP can be labeled, immobilizing the other with detection of label upon the immobilized substrate directly (as in a radiolabel) or in a coupled assay, as in known in the art. In another example, the inhibition can be detected by observing the absence or inhibition of TRAF-1, TRAF-2, or TRAF-3 activity, such as the absence of NF-κB activity. In yet another embodiment, the inhibition can be determined by observing decreased cell proliferation. Alternatively, phosphate or ATP can be observed, indicating the presence of dephosphorylation activity. Sensitive assays for detecting the presence of phosphate or ATP are very well known in the art, including luciferin/luciferase coupled assays.

Alternatively, $HT_{m4}$ antagonists can be screened by contacting $HT_{m4}$ with a native ligand of $HT_{m4}$ and detecting the absence of binding. Binding in this embodiment can be detected in a similar manner as above, including the use of radiolabels and substrates for immobilization or the observation of cell proliferation or NF-κB transcription activation.

In detecting agonists, $HT_{m4}$ can be contacted with KAP, TRAF-1, TRAF-2, TRAF-3 or a native ligand of $HT_{m4}$, as described above. Agonists can possess one or more of the properties of increasing NF-κB gene transcription, cell proliferation, or TRAF-1, TRAF-2, or TRAF-3 activity or decreasing KAP dephosphorylation activity. Detection of one or more of these properties can be determined in the same manner as described above for antagonists.

$HT_{m4}$ antagonists are defined herein as molecules or proteins which decrease or inhibit (including competitive inhibition) one or more biological activities of $HT_{m4}$. $HT_{m4}$ agonists are defined herein as molecules or proteins which increase or activate one or more biological properties of $HT_{m4}$. $HT_{m4}$ biological properties or activities include, for example, cell proliferation and TRAF-2 activation. Agonists and antagonists, together, are considered modulators. Examples of compounds which can be antagonists or agonists (depending upon their antigen binding sites) include antibodies which bind $HT_{m4}$, a native ligand of $HT_{m4}$, KAP, TRAF-1, TRAF-2 and TRAF-3. Other examples include fragments or variants of $HT_{m4}$, KAP, TRAF-1, TRAF-2, TRAF-3 and a native ligand of $HT_{m4}$. Particularly preferred embodiments of the present invention include antibodies which bind $HT_{m4}$ and $HT_{m4}$ fragments and variants. Fragments and variants of $HT_{m4}$ which possess substantial sequence identity to the relevant binding site of $HT_{m4}$ but do not possess other active or binding sites of the protein are examples of useful modulators.

The methods of screening can be accomplished under known conditions suitable for binding of $HT_{m4}$ and binding partners (e.g. a native ligand of $HT_{m4}$, KAP, TRAF-1, TRAF-2 and TRAF-3). Generally, physiological conditions can be employed, including cellular pH. As is known in the art, the presence of buffers can effectively control the pH of a reaction medium. Temperature of the reaction can generally be any temperature at which substantial denaturation of the protein does not occur. Room temperature can generally be suitably employed.

It can be particularly advantageous to conduct the assay in a cellular system. In such an embodiment, a cell or cells which express $HT_{m4}$ a native ligand of $HT_{m4}$, KAP and/or TRAF-1, TRAF-2, TRAF-3(including hematopoietic cells or cells which possess a recombinant construct containing DNA which encodes these proteins) is contacted with the compound to be screened. In one embodiment, the cells can be viable or inviable, whole or lysed during one or more steps of the method. It can be particularly advantageous to employ cells which further comprise a reporter gene, such as the P-galactosidase gene, under control of the NF-κB promoter, which is activated by $HT_{m4}$. In this method, inhibitors and activators of $HT_{m4}$ can be determined by observing the expression of the reporter gene.

Where the assay is determining the modulation of $HT_{m4}$ activity in the cytoplasm of the cell, it is generally desirable to select compounds for screening which can be introduced or delivered into the cytoplasm. To facilitate delivery to the cytoplasm, the compound or agent can be added to the reaction medium in a vehicle which permits transfer across the cell membrane, such as in a liposome. Proteins can also be delivered to the cytoplasm of the membrane via a vector, which upon transfection, causes expression of the protein.

The present invention will now be illustrated by the following examples, which are not intended to be limiting in any way.

EXAMPLE I

Materials and Methods

Cell Lines and Primary Cells: Hematopoietic cell lines used in this study included lymphomyeloid (DU528), erythroleukemic (K562,OCIR), promyelocytic (HL60), myeloblastic (KG-1), monoblastic (U937), T-cell leukemia/lymphoma (MOLT-4, Ly17, Ly13) and myeloma (OCI-My5) lines. Non-hematopoietic cell lines used included bone marrow stromal (BS-1), hepatoma (HepG2), melanoma (HS294), skeletal muscle (HuSk), neuroblastoma (SKNSH), cervical cancer (HeLa) and lung cancer (Calu-1) cells. All cell lines were maintained in Iscovels modified Dulbecco's medium supplemented with 10% fetal bovine serum and 1 mM L-glutamine, except for DU528, in which horse serum replaced bovine serum. Total RNAs from a human mast cell line, HMC-1 (Butterfield, J. H. et al., *Leuk. Res.* 12:345–355 (1988)), and a human factor dependent megakaryocytic line, M07e, were kindly provided by Dr. Karl Nocka, Cytomed Inc., Cambridge, Mass. Normal bone-marrow cells were harvested from transfusion-filters after bone marrow transplantations. Primary leukemic cells with over 90% blasts were harvested from the peripheral blood of a patient with M4 acute myeloid leukemia. Total RNAs of neutrophils and eosinophils from normal individuals and eosinophils from a patient with hypereosinophilic syndrome were kindly provided by Dr. Peter Weller and Dr. Kaiser Lim, Harvard Medical School.

Preparation of Probes from Subtractive cDNA Libraries for Differential Screening: The construction of four subtractive cDNA libraries (DU528/BS-1, K562/BS-1, KG-l/BS-1, and BS-1/BS-1), from three human hematopoietic cell lines (DU528, K562 and KG-1) and one non-hematopoietic human cell line (BS-1), using the PT3T719U multiphagemid vector (Pharmacia) was described previously (Lelias, J. M. et al., *Proc. Natl. Acad. Sci. USA* 90:1479–1483 (1993)). cDNA inserts released from two of the hematopoietic (DU528/BS-1 and KG-l/BS-1) and the non-hematopoietic (BS-1/BS-1) subtractive libraries were purified, labeled with $^{32}P$, and used as probes to screen the K562/BS-1 library (Sambrook, J. et al., *Molecular Cloning: A Laboratory Manual,* 2nd edition (Cold Spring Harbor Lab., Cold Spring Harbor, N.Y. (1989)).

Induction of Cell Line U937: The U937 cell line was grown to a concentration of 5×10 cells per ml and differentiation was induced with 50 nM phorbol 12-myristate 13-acetate (PMA; Sigma).

Chromosomal Localization of the $HT_{m4}$ Gene: The chromosomal location of the $HT_{m4}$ gene was determined by fluorescent in situ hybridization (FISH) as previously described (Kobayashi, H. et al., *Blood* 81:3027–3033 (1993)). Human metaphases were prepared from phytohemagglutinin-stimulated peripheral blood lymphocytes. The $HT_{m4}$ cDNA was labeled by nick-translation with biotin-11-UTP (Enzo Diagnostics, Syosset, N.Y.). The biotin-labeled probe was hybridized to metaphase cells and detected with fluorescein-conjugated avidin (Vector Lab, Burlingame, Calif.). Slides were examined by two independent observers without knowledge of the probe used.

Reverse-transcriptase Polymerase Chain Reaction (RT-PCR)

Reverse transcriptase reaction was carried out as described (Sanger, F. et al., *Proc. Natl. Acad. Sci. USA* 74:5463–5467 (1977)) with RNAs from cell lines or cells enriched for various cell types to obtain first strand cDNAs. The cDNAs were subjected to PCR amplification reactions as described (Wulf, G. M. et al., *EMBO J.* 12:5065–5074 (1993)), using primers spanning nucleotide 721 to 1087 of $HT_{m4}$ to give a predicted PCR product of 388 nucleotides. The sense primer used was 5'-TCACCTCCCAATTCTGTGTAATCAAGA-3' (SEQ ID NO: 1), and the anti-sense primer was 5'-GATTATACCGCCTTCGTTCCTTA AACC-3'(SEQ ID NO: 2). PCR reactions were carried out with 100 nM primers for 30 cycles of denaturation (1 minute at 94° C.), annealing (1 minute at 54° C.) and extension (2 minutes at 72° C.).

General Methods: RNA was isolated using the RNAzol method (Biotecx Laboratories, Houston, Tex.). DNA sequencing was done by the dideoxynucleo-tide chain-termination technique (Sanger, F. et al., *Proc. Natl. Acad. Sci. USA* 74:5463–5467 (1977)) after subcloning appropriate DNA fragments into M13.

Results

Isolation of Clone $HT_{m4}$: By differential screening of the K562 hematopoietic library with cDNA probes from two hematopoietic libraries (enriched for hematopoietic cDNAs) and cDNA probes from the non-hematopoietic BS-1 library, clones that hybridized positively only to the hematopoietic probes were isolated. One of these, denoted clone $HT_{m4}$ was used as a probe to screen a Northern blot panel consisting of total RNAs from various hematopoietic and non-hematopoietic cell lines.

Expression pattern of $HT_{m4}$: A combination of Northern blot and RT-PCR analysis was used to determine the spectrum of tissue and lineage expression of the gene. The cDNA insert of clone $HT_{m4}$ hybridized to a transcript of about 1.7 kb in five hematopoietic lines which included myeloid and erythroid lineages and to normal human bone marrow cells. The $HT_{m4}$ and mRNA was not detectable in a T cell lymphoma line (Ly17) and in a lymphomyeloid leukemic line with T and granulocytic differentiation potential (DU528). In all of the seven non-hematopoietic cell lines which included lung, cervical, brain, skeletal muscle, melanoma, hepatoma, and bone marrow stromal cells, no hybridizing mRNA could be detected. These non-hematopoietic lines included cells of ectodermal, endodermal and mesodermal origin. The mRNA was also absent in the primary blast cells of a patient diagnosed to have M4 acute myeloid leukemia (AML).

To facilitate screening of RNA samples, particularly those derived from cells in quantities too limited for Northern blot analysis, we examined expression by RT-PCR. The quality of the first strand cDNAs obtained after reverse transcription was satisfactory as evaluated by using primers for the housekeeping gene HPRT. Based on nucleotide sequence of $HT_{m4}$ cDNA, oligonucleotides were synthesized and used as specific primers for PCR amplification. The predicted PCR product of a 388 nucleotide-long DNA was obtained in normal bone marrow cells and the HL60 cell line but not in the HeLa and Ly17 cell line, confirming the Northern blot analysis. RNAs from a human mast cell line (HMC-1) and a megakaryocytic line (MO7e) were also positive for $HT_{m4}$ mRNA. RNAs from normal eosinophils or neutrophils and eosinophils from a patient with hyper-eosinophilic syndrome (HES) also yielded the predicted PCR product. Two leukemic T-cell lines (Ly13 and MOLT4) and a myeloma cell line (OCI-My5) were also found to be positive for $HT_{m4}$. All PCR-derived DNAs hybridized positively to radio-labeled $HT_{m4}$ in subsequent Southern analysis.

Molecular analysis of $HT_{m4}$ human cDNA: The nucleotide sequence of the $HT_{m4}$ cDNA and the predicted amino acid sequence are shown in FIGS. 1A and 1B. The 1672-nucleotide long cDNA contains a long open reading frame, beginning at nucleotide position 97, encoding a protein of 214 amino acids with a calculated molecular mass of 25 kDa. A hydrophilicity analysis with the Kyte-Doolittle algorithm (Kyte, J. and Doolittle, R. F. *J. Mol. Biol.* 157:105–132 (1982)), reveals that $HT_{m4}$ contains four hydrophobic domains of 20 to 21 amino acids. The amino terminal region before the beginning of the first hydrophobic domain contains four prolines. Each of the hydrophilic regions between the transmembrane segments contains a single proline. Several substrates for Casein kinase 2 phosphorylation (Pina, L. a. *Biochim . Biophys. Acta* 1054:267–284 (1990)) of serine/threonine are found at residues 24 (TGPE), 155 (SSSE), 181 (TLLE), and 203 (SREE) and for Protein Kinase C phosphorylation at residue 149 (SLR). The sequence is consistent with a polypeptide chain that crosses the membrane four times, projecting two small loops extracellularly, and retaining the amino- and carboxyl-terminal portions in the cytoplasm.

Expression of $HT_{m4}$ during differentiation of cell line U937: To ascertain if expression of the $HT_{m4}$ mRNA may vary depending on the stage of cellular differentiation, we examined the consequences of induced differentiation in the monoblastic cell line U937. Exposure of the cells to PMA rapidly induced differentiation to macrophages, as confirmed morphologically and molecularly by monitoring the marker for terminally differentiated macrophages, CD11b (Arnout, M. A. *Immunol. Rev.* 114:145–180 (1990)). The expression of $HT_{m4}$ mRNA over a period of 48 hours showed an initial increase followed by a down regulation so that by day three, $HT_{m4}$ transcripts were detectable at a very low level.

$HT_{m4}$ is located on chromosome 11q12–13: Forty-one chromosomes from 30 metaphases were scored for the positive chromosomal band. Band 11q12 was labeled on eighteen of chromosome 11 homologues, band 11q13.1 on twenty-one of chromosome 11 homologues and band 11q13.2 on two of chromosome 11 homologues. No signal was detected on other chromosomes in these cells. Similar results were obtained in an additional experiment using this probe. Thus, $HT_{m4}$ is localized to chromosome 11q12–q13.1.

EXAMPLE II

To search for target proteins that interact with $HT_{m4}$, a double hybrid yeast cloning system was utilized. See Fields, S. and Song, O., *Nature* 34:245, the teachings of which are incorporated herein by reference in their entirety.

A fusion protein, vector, LexA-75$HT_{m4}$, was constructed fusing the LexA DNA-binding domain to the last 75 amino acids of the carboxyl terminus of $HT_{m4}$. The LexA binding domain binds to the GAL4-activating domain (GAD) and is used frequently as an alternative to the GAL4 binding domain. The LexA-$HT_{m4}$ construct was to sequenced to ensure that the $HT_{m4}$ fragment was properly in frame with no mutation. The $HT_{m4}$ portion included the fourth hydrophilic transmembrane domain and the cytoplasmic hydrophilic carboxyl terminus. LexA-75$HT_{m4}$ DNA was co-transformed with DNA from a day 13 rat embryonic GAD-cDNA library into a HIS3/LacZ yeast strain. In the absence of histidine selection, about 15 million transformants were obtained, indicating a very high transfection efficiency. In the presence of histidine selection, about 20 yeast clones prototrophic for histidine were obtained. These colonies surviving in the histidine-minus plates indicate the presence of proteins from a co-transfected clone interacting with $HT_{m4}$ and activating the histidine gene in the yeast recipient strain. Testing of these clones for β-galactosidase activity showed that 90% of the colonies gave a positive blue reaction from very strong blue (70%) to light blue. Only about 10% were negative, indicating a very effective pre-selection with the histidine. In a preliminary analysis, plasmid DNA from 15 strongly blue yeast clones were transformed in bacteria, selected in leu plates for cDNA and 4–5 colonies picked for each yeast clone. DNA from each plasmid was then independently transformed with the LexA-$HT_{m4}$ DNA into yeast to see which clone was responsible for the β-galactosidase activity. Two classes of proteins specifically interacting with $HT_{m4}$ were identified.

KAP The first clone that was isolated, designated HT4BP-1, contains a 311 bp partial cDNA with 85% identity to a human cDNA called KAP (CDK2 Associated Protein), a dual-specific phosphatase. HT4BP-1 contains a long open reading frame of 103 amino acids corresponding to the carboxyl end of the KAP protein. It is significant that within this region is the HCXXXXGR motif characteristic of the catalytic core of protein tyrosine phosphatases. To check for specificity of interaction between HT4BP-1/KAP and $HT_{m4}$, HT4BP-1 was transfected with LexA-Lamin and LexA-MEK (a kinase protein). No colonies were obtained on LTH plates. In contrast when HT4BP-1 was cotransfected with LexA-75$HT_{m4}$, a large number of colonies was obtained. When these individual colonies were patched and tested for β-Galactosidase activity, they all gave a strong positive blue reaction. LexA-75$HT_{m4}$ transfected by itself or with GAD-byr, GAD-MEK, GAS-ras and GAD-rac did not give any colonies. These results indicate a very specific binding between $HT_{m4}$ and KAP.

To test for the KAP binding domain in LexA-75$HT_{m4}$, deletions were made of the LexA-$HT_{m4}$ bait. The LexA-$HT_{m4}$ tail was truncated to remove the transmembrane 4 domain to give a bait LexA-25$HT_{m4}$ consisting of only the last 25 amino acids of the hydrophilic cytoplasmic tail. LexA-25$HT_{m4}$ on its own gave no colonies, but with HT4BP-1/KAP it gave a large number of colonies, all of which gave a positive β-Gal activity. Thus it appears that in the two-hybrid assay, the hydrophilic tail of $HT_{m4}$ alone is sufficient to allow binding to KAP protein.

TRAF-2 HT4BP-3 is a 336 bp cDNA with 87% identity to TRAF-2. The cDNA clone contains a long open reading frame of 109 amino acids. This region corresponds to a region in the carboxyl end of the TRAF-2 protein amino acid in which resides the TRAF motif. A second cDNA clone, HT4BP-2, containing the same overlapping cDNA as HT4BP-3 was isolated from a different blue yeast colony. Clone HT4BP-2/TRAF-2 transfected with LexA-75$HT_{m4}$ gave rise to a dense number of colonies, all of which tested a strong blue-positive for β-gal activity. HT4BP-3/TRAF-2 cotransfected with LexA-Lamin or LexA-MEK resulted in colony growth at a frequency significantly lower than with $HT_{m4}$. These results indicate clearly a preferential binding between TRAF-2 and the $HT_{m4}$ carboxyl terminus.

To test whether $HT_{m4}$ binds also to two other TRAF like proteins, TRAF-1 and TRAF-3, TRAF-1 was isolated at the same time as TRAF-2 and the two TRAFs were thought to bind together as a complex with the TNF receptor tail. TRAF-3 was isolated as a protein binding to the cytoplasmic tail of the EBV transforming protein, late membrane protein (LMP-2). The protocol set forth in Song and Fields, infra, was repeated with GAD vectors. The GAD-TRAF1 and GAD-TRAF3 vectors were kindly provided by Drs. George Mosialos and Elliot Kief, Harvard. Surprisingly, while LexA-75 $HT_{m4}$ binds to TRAF-2, it does not interact with TRAF-1 nor TRAF-3. However, the truncated tail minus the transmembrane 4 domain, LexA-25 $Ht_{m4}$, binds very well with TRAF-1 and TRAF-3.

Equivalents

Those skilled in the art will know, or be able to ascertain, using no more than routine experimentation, many equivalents to the specific embodiments of the invention described herein. These and all other equivalents are intended to be encompassed by the following claims.

We claim:

1. An isolated recombinant DNA molecule comprising extrachromosomal DNA encoding the carboxyl terminus of a mammalian $HT_{m4}$ protein, said carboxyl terminus corresponding to amino acid residues 193–214 of human $HT_{m4}$ protein consisting of SEQ ID NO:4.

2. The DNA molecule of claim 1, wherein said extrachromosomal DNA consists of nucleotides 673–738 of SEQ ID NO:3.

3. The DNA molecule of claim 1, wherein the extrachromosomal DNA encodes amino acid residues 193–214 of a human $HT_{m4}$ protein consisting of SEQ ID NO:4.

4. An isolated recombinant DNA molecule comprising cDNA encoding the carboxyl terminus of a mammalian $HT_{m4}$ protein, said carboxyl terminus corresponding to amino acid residues 193–214 of human $HT_{m4}$ protein consisting of SEQ ID NO:4.

5. A DNA vector comprising the sequence of nucleotides 673–738 of SEQ ID NO.: 3.

6. A transfected host cell which has been stably transfected with a recombinant DNA molecule according to claim 1.

7. A transfected host cell which has been stably transfected with a recombinant DNA molecule according to claim 2.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (xi) SEQUENCE DESCRIPTION: SEQ ID NO:1:

TCACCTCCCA ATTCTGTGTA ATCAAGA                                                  27

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (xi) SEQUENCE DESCRIPTION: SEQ ID NO:2:

GATTATACCG CCTTCGTTCC TTAAACC                                                  27

(2) INFORMATION FOR SEQ ID NO:3:

(i) SEQUENCE CHARACTERISTICS:
      (A) LENGTH: 1661 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 97..738

(xi) SEQUENCE DESCRIPTION: SEQ ID NO:3:

GTGATCTTTT CTGAGTGTCT CCTACTTGCG ACAAGGTGGA CTTGGGAGGA AAGCCGTCTG     60

CCAAAGCCTG AAGCCTCCAA GCCATAAACA ACCCCA ATG GCC TCC CAC GAA GTT     114

```
                         Met Ala Ser His Glu Val
                          1               5
GAT AAT GCA GAG CTG GGG TCA GCC TCT GCC CAT GGT ACC CCA GGC AGT        162
Asp Asn Ala Glu Leu Gly Ser Ala Ser Ala His Gly Thr Pro Gly Ser
             10                  15                  20

GAG ACG GGA CCA GAA GAG CTG AAT ACT TCT GTC TAC CAC CCC ATA AAT        210
Glu Thr Gly Pro Glu Glu Leu Asn Thr Ser Val Tyr His Pro Ile Asn
             25                  30                  35

GGA TCA CCA GAT TAT CAG AAA GCA AAA TTA CAA GTT CTT GGG GCC ATC        258
Gly Ser Pro Asp Tyr Gln Lys Ala Lys Leu Gln Val Leu Gly Ala Ile
         40                  45                  50

CAG ATC CTG AAT GCA GCA ATG ATT CTG GCT TTG GGT GTC TTT CTG GGT        306
Gln Ile Leu Asn Ala Ala Met Ile Leu Ala Leu Gly Val Phe Leu Gly
 55              60                  65                      70

TCC TTG CAA TAC CCA TAC CAC TTC CAA AAG CAC TTC TTT TTC TTC ACC        354
Ser Leu Gln Tyr Pro Tyr His Phe Gln Lys His Phe Phe Phe Phe Thr
                 75                  80                  85

TTC TAC ACA GGC TAC CCG ATT TGG GGT GCT GTG TTT TTC TGT AGT TCA        402
Phe Tyr Thr Gly Tyr Pro Ile Trp Gly Ala Val Phe Phe Cys Ser Ser
                 90                  95                 100

GGA ACC TTG TCT GTT GTA GCA GGG ATA AAA CCC ACA AGA ACA TGG ATA        450
Gly Thr Leu Ser Val Val Ala Gly Ile Lys Pro Thr Arg Thr Trp Ile
             105                 110                 115

CAG AAC AGT TTT GGA ATG AAC ATT GCC AGT GCT ACA ATT GCA CTA GTG        498
Gln Asn Ser Phe Gly Met Asn Ile Ala Ser Ala Thr Ile Ala Leu Val
             120                 125                 130

GGG ACT GCT TTT CTC TCA CTA AAT ATA GCA GTT AAT ATC CAG TCA TTA        546
Gly Thr Ala Phe Leu Ser Leu Asn Ile Ala Val Asn Ile Gln Ser Leu
135             140                 145                 150

AGG AGT TGT CAC TCT TCA TCA GAG TCA CCG GAC CTA TGC AAT TAC ATG        594
Arg Ser Cys His Ser Ser Ser Glu Ser Pro Asp Leu Cys Asn Tyr Met
                 155                 160                 165

GGC TCC ATA TCA AAT GGC ATG GTG TCT CTA CTG CTG ATT CTC ACC TTG        642
Gly Ser Ile Ser Asn Gly Met Val Ser Leu Leu Leu Ile Leu Thr Leu
             170                 175                 180

CTG GAA TTA TGC GTA ACT ATC TCT ACC ATA GCC ATG TGG TGC AAT GCA        690
Leu Glu Leu Cys Val Thr Ile Ser Thr Ile Ala Met Trp Cys Asn Ala
     185                 190                 195

AAC TGC TGT AAT TCA AGA GAG GAA ATT TCC TCA CCT CCC AAT TCT GTG        738
Asn Cys Cys Asn Ser Arg Glu Glu Ile Ser Ser Pro Pro Asn Ser Val
200                 205                 210

TAATCAAGAA TACCTCCTTA TGAAAATAAT TCTGAGAGCA TGAATATTTG ACCTTAAATC      798

TCCAGTGACT CAGAGCTTCA CCCACAAACT CAGGAGAACA TAAGCCTGCT CGTAAAGCTC      858

AATCCTTCTA TCATGGCACC AATCACAAGA ACCTGGACG TTTGACTGAC TCTATCCTTT       918

CTCTCCTAAC TATAAATCCT ATTTGTGTGT CGTGGGTATG GAAGGACAGA TATATTTCTT      978

TAGGCATTCT TGGATATCTG TAACTTCTAT GATCATTACT CCAAAGTTGT TTCCAGAAAT     1038

TGGTTCTATT TCTTCTTATC CACCTACTCC ATTGCTTTAT GAGGTTTAAG GAAGGAAGGC     1098

GGTATAATCC CTATTCAATA TATTTTTTCT AAAATCCAAC TTCTGACCGC CCAGTAGGAA     1158

GAAAAATGAG ACATTTTTTC CATTACAGAG AAATGCTTCT TGACTTTAAC ATCAGCATTA    1218

TAAAAAGTGT CAAATAAAAA ATTACCATCA TTATCATTAA AATAAATTTT CACTGTATTT    1278

GAGATGGGAG GGTAAGGCT CAGGGATTTT ATTTCAGTGA ACTGCTGGAA CTCACACATG     1338

CCCTGATATG TAAATGATGA TTTATGTTGG CGAGTCTGAG AGCAAGCCCA AATGTGTTCT    1398

TCAAAGGACA ATGGGAAACT GTAAAGTAGA GAACTAAAGA ATAAGGCCTT TAGAATCTGA   1458

CACATCTGGG TTCAAATTCT GAAACTGTCA CTTATTACCT GTATGAACAT GGGCAAATTA  1518
```

-continued

```
TCTAATCTCT CTGATCTATT TTTCCTCATC TGTAAAATAG GTGTAATAAT AACAACTACT      1578

TTGTCGGTTG CTCTGAGGGT TAAATGAAAA TAAAAAGAAA ATGTGAAACA GCACCACAGG      1638

TACTTGAAAA AAAAAAAAAA AAA                                              1661
```

(2) INFORMATION FOR SEQ ID NO:4:

(i) SEQUENCE CHARACTERISTICS:
        (A) LENGTH: 214 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser His Glu Val Asp Asn Ala Glu Leu Gly Ser Ala Ser Ala
 1               5                  10                  15

His Gly Thr Pro Gly Ser Glu Thr Gly Pro Glu Glu Leu Asn Thr Ser
            20                  25                  30

Val Tyr His Pro Ile Asn Gly Ser Pro Asp Tyr Gln Lys Ala Lys Leu
        35                  40                  45

Gln Val Leu Gly Ala Ile Gln Ile Leu Asn Ala Ala Met Ile Leu Ala
    50                  55                  60

Leu Gly Val Phe Leu Gly Ser Leu Gln Tyr Pro Tyr His Phe Gln Lys
65                  70                  75                  80

His Phe Phe Phe Thr Phe Tyr Thr Gly Tyr Pro Ile Trp Gly Ala
                85                  90                  95

Val Phe Phe Cys Ser Ser Gly Thr Leu Ser Val Val Ala Gly Ile Lys
                100                 105                 110

Pro Thr Arg Thr Trp Ile Gln Asn Ser Phe Gly Met Asn Ile Ala Ser
            115                 120                 125

Ala Thr Ile Ala Leu Val Gly Thr Ala Phe Leu Ser Leu Asn Ile Ala
            130                 135                 140

Val Asn Ile Gln Ser Leu Arg Ser Cys His Ser Ser Ser Glu Ser Pro
145                 150                 155                 160

Asp Leu Cys Asn Tyr Met Gly Ser Ile Ser Asn Gly Met Val Ser Leu
                165                 170                 175

Leu Leu Ile Leu Thr Leu Leu Glu Leu Cys Val Thr Ile Ser Thr Ile
                180                 185                 190

Ala Met Trp Cys Asn Ala Asn Cys Cys Asn Ser Arg Glu Glu Ile Ser
            195                 200                 205

Ser Pro Pro Asn Ser Val
        210
```